(12) United States Patent
Nanjo

(10) Patent No.: US 6,729,727 B2
(45) Date of Patent: May 4, 2004

(54) OPHTHALMIC PHOTOGRAPHING APPARATUS

(75) Inventor: Tsuguo Nanjo, Toyohashi (JP)

(73) Assignee: Nidek Co., Ltd., Aichi-Ken (JP)

( * ) Notice: Subject to any disclaimer, the term of this patent is extended or adjusted under 35 U.S.C. 154(b) by 94 days.

(21) Appl. No.: 10/211,319

(22) Filed: Aug. 5, 2002

(65) Prior Publication Data

US 2003/0025876 A1 Feb. 6, 2003

(30) Foreign Application Priority Data

Aug. 6, 2001 (JP) ........................................ 2001-238368

(51) Int. Cl.⁷ .............................. A61B 3/14; A61B 3/10
(52) U.S. Cl. ........................ 351/206; 351/214; 351/221; 396/18
(58) Field of Search ................................ 351/200, 205, 351/206, 214–216, 221, 246; 396/18

(56) References Cited

U.S. PATENT DOCUMENTS

| | | | |
|---|---|---|---|
| 5,508,760 A | 4/1996 | Kobayashi et al. | |
| 5,638,150 A | 6/1997 | Doherty | |
| 5,668,621 A | 9/1997 | Nanjo | |
| 5,742,374 A | 4/1998 | Nanjo et al. | |
| 5,757,462 A | 5/1998 | Nanjo | |
| 5,757,463 A * | 5/1998 | Kohayakawa | 351/214 |
| 6,033,075 A * | 3/2000 | Fujieda et al. | 351/212 |
| 6,361,167 B1 * | 3/2002 | Su et al. | 351/206 |
| 6,364,484 B2 * | 4/2002 | Yamada | 351/200 |
| 2002/0003608 A1 * | 1/2002 | Yamada | 351/245 |
| 2002/0060778 A1 * | 5/2002 | Su et al. | 351/206 |

FOREIGN PATENT DOCUMENTS

| | | |
|---|---|---|
| JP | A 6-245906 | 9/1994 |
| JP | A 10-234673 | 9/1998 |
| JP | A 11-513591 | 11/1999 |

OTHER PUBLICATIONS

U.S. patent application Ser. No. 08/960,825, Nanjo, filed Oct. 30, 1997.

* cited by examiner

*Primary Examiner*—Dennis W. Ruhl
*Assistant Examiner*—John R Sanders
(74) *Attorney, Agent, or Firm*—Oliff & Berridge, PLC (57) ABSTRACT

An ophthalmic photographing apparatus capable of photographing a fundus and a slit-sectioned anterior segment of an eye in non-mydriatic conditions. The apparatus is provided with a light source unit including an infrared light source optical system for observation and a visible light source optical system for photographing, a hand-held photographing unit including a first illumination optical system with an illumination lens, and an observation/photographing optical system with an objective lens, and being separated from the light source unit, a slit light illumination unit including a second illumination optical system with a slit plate and an illumination lens, and being removably attached to the photographing unit, and a photoconductive tube connecting the light source unit to the photographing or illumination unit and transmitting infrared light for observation and visible light for photographing from the light source unit to the first or second illumination optical system.

10 Claims, 6 Drawing Sheets

OPHTHALMIC PHOTOGRAPHING APPARATUS

BACKGROUND OF THE INVENTION

1. Field of the Invention

The present invention relates to an ophthalmic photographing apparatus for photographing a fundus and photographing a slit-sectioned anterior segment of an eye to be examined.

2. Description of Related Art

As hand-held fundus cameras, those of mydriasis photographing type and non-mydriasis photographing type are known. In the former, a fundus may be observed under visible illumination light for observation to be photographed in color with a mydriatic administered to an eye. In the latter, a fundus is observed under infrared illumination light for observation to be photographed in color without a mydriatic administered to an eye. Administering a mydriatic places a burden on an eye to be examined, for example, by making the eye so sensitive to light that it is almost blinded in bright light for a while.

It should be noted that, in an ophthalmic examination, it is sometimes necessary to photograph not only a fundus but also a slit-sectioned anterior segment of an eye. However, this requires an examiner to prepare and use a photographing apparatus other than a fundus camera, which is inconvenient for the examiner. In addition, it will be convenient if other parts of an eye than its fundus may be photographed under non-mydriatic conditions.

SUMMARY OF THE INVENTION

The present invention has been made in view of the above circumstances and has an object to overcome the above problems and to provide an ophthalmic photographing apparatus capable of photographing a fundus and a slit-sectioned anterior segment of an eye under non-mydriatic conditions.

To achieve the objects and in accordance with the purpose of the present invention, as embodied and broadly described herein, an ophthalmic photographing apparatus is provided with a light source unit, a hand-held photographing unit, a slit light illumination unit, and a photoconductive tube. Placed in the light source unit are an infrared illumination light source optical system for observation and a visible illumination light source optical system for photographing. Placed in the photographing unit are a first illumination optical system with an illumination lens and an observation/photographing optical system with an objective lens. The photographing unit is separated from the light source unit. Placed in the illumination unit is a second illumination optical system with a slit plate and an illumination lens. The illumination unit is removably attached to the photographing unit. The photoconductive tube connects the light source unit selectively to the photographing unit and the illumination unit, and transmits infrared illumination light for observation and visible illumination light for photographing from the light source unit selectively to the first illumination optical system and the second illumination optical system. The observation/photographing optical system is used to observe and photograph a fundus of an eye to be examined which is illuminated by the infrared illumination light for observation and the visible illumination light for photographing via the first illumination optical system, and to observe and photograph an anterior segment of the eye illuminated by the infrared illumination light for observation and the visible illumination light for photographing via the second illumination optical system.

In another aspect of the present invention, an ophthalmic photographing apparatus is provided with a light source unit, a hand-held photographing unit, a slit light illumination unit, and a photoconductive tube. Placed in the light source unit is a visible illumination light source optical system for photographing. Placed in the photographing unit are an infrared illumination light source optical system for observation, a first illumination optical system with an illumination lens, and an observation/photographing optical system with an objective lens. The photographing unit is separated from the light source unit. Placed in the illumination unit is a second illumination optical system with a slit plate and an illumination lens. The illumination unit is removably attached to the photographing unit. The photoconductive tube connects the light source unit selectively to the photographing unit and the illumination unit, and transmits visible illumination light for photographing from the light source unit selectively to the first illumination optical system and the second illumination optical system. The observation/photographing optical system is used to observe and photograph a fundus of an eye to be examined, which is illuminated by the infrared illumination light for observation and the visible illumination light for photographing via the first illumination optical system. The observation/photographing optical system is also used to observe an anterior segment of the eye illuminated by the infrared illumination light for observation via the first illumination optical system, and to photograph the anterior segment illuminated by the visible illumination light for photographing via the second illumination optical system.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
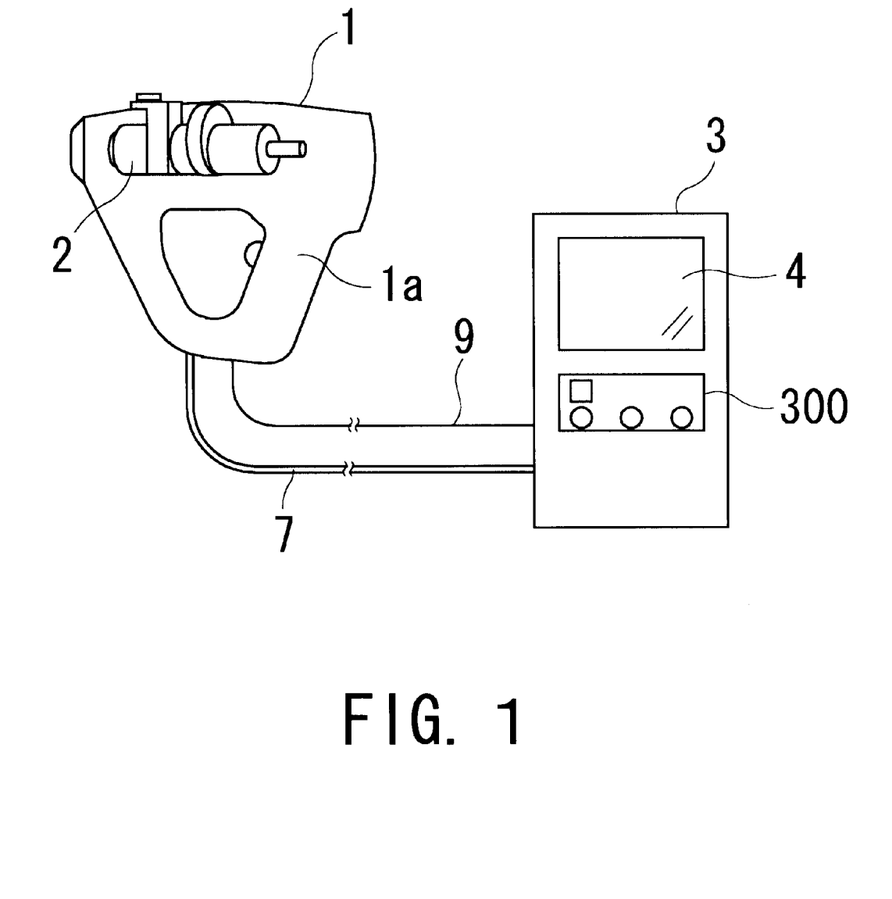
FIG. 1 shows a schematic configuration of an ophthalmic photographing apparatus according to the present invention.

A detailed description of one preferred embodiment of an ophthalmic photographing apparatus embodying the present invention will now be given referring to the accompanying drawings. FIG. 1 shows a schematic configuration of the ophthalmic photographing apparatus according to the present invention. The ophthalmic photographing apparatus is roughly constituted of a hand-held photographing unit 1, a slit light illumination unit 2 attachable to and detachable from the photographing unit 1, and a control unit (a light source unit) 3. The photographing unit 1 is provided with a grip part 1a that an examiner can hold with one hand. The control unit 3 is provided with illumination light sources 11 and 15, a color monitor 4 for displaying an observed image and a photographed image, a control panel 300, and the like, which are to be described later. An optical fiber (a fiber bundle) 7 transmits illumination light from the control unit 3 to an illumination optical system in the photographing unit 1 and that in the illumination unit 2. A communication cable 9 connects the photographing unit 1 and the control unit 3.

Figure 2:
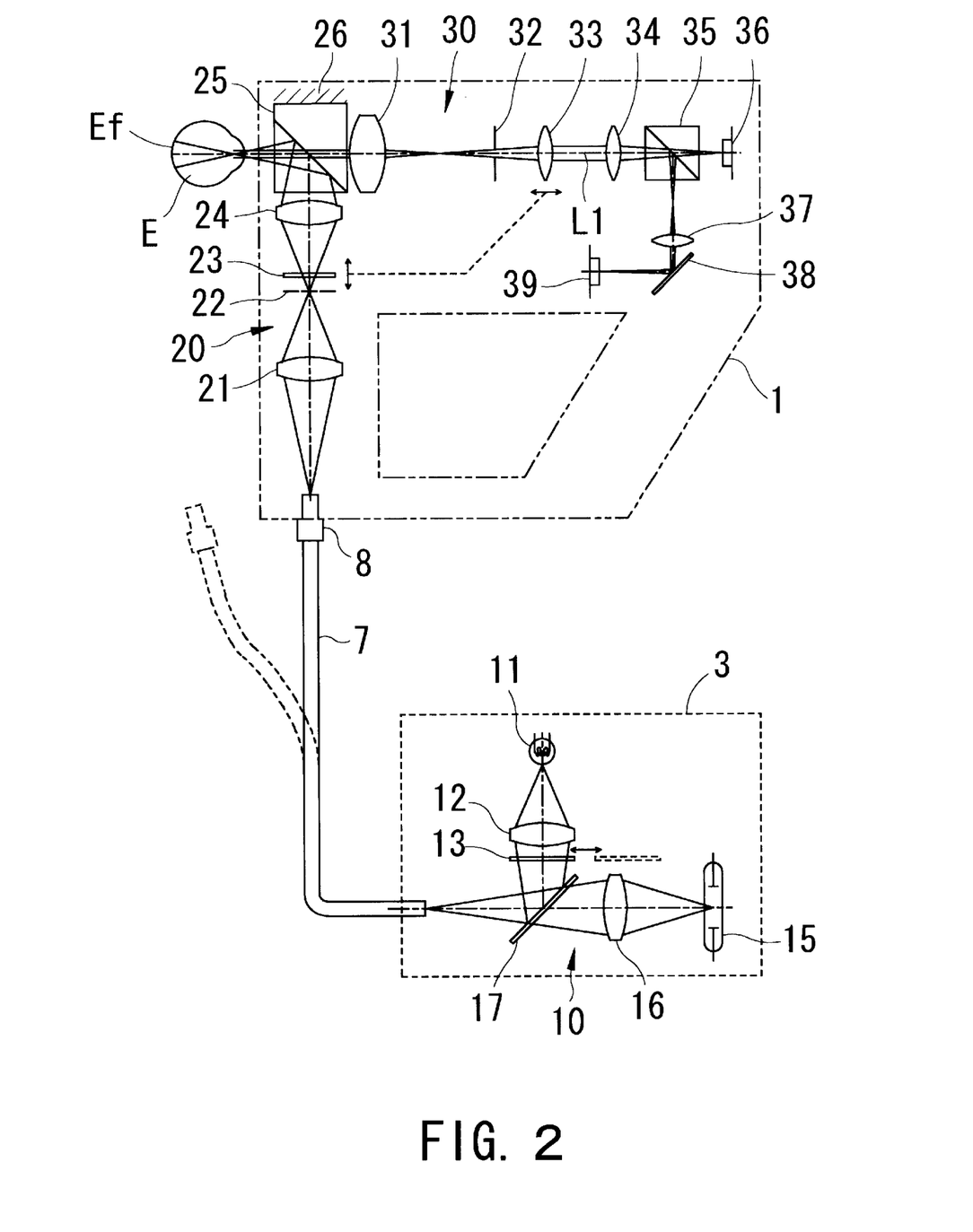
FIG. 2 shows a schematic configuration of optical systems in a photographing unit and in a control unit.
Figure 3:
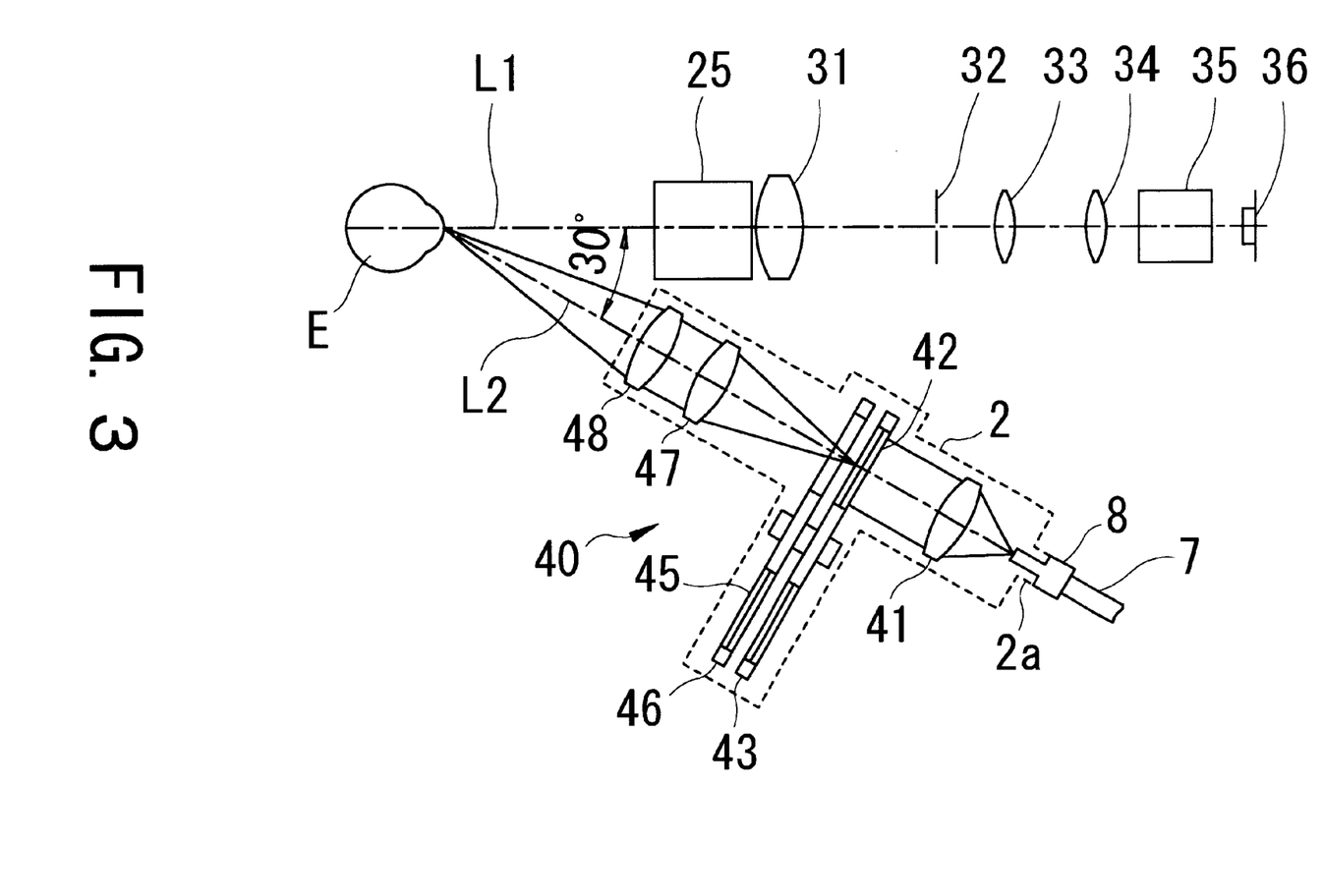
FIG. 3 shows an optical system in a slit light illumination unit.

FIG. 2 shows the optical systems in the photographing unit 1 and in the control unit 3. FIG. 3 shows the optical system in the illumination unit 2.

<Illumination Light Source Optical System>

Arranged in the control unit 3 is an illumination light source optical system 10 constituted of a halogen lamp 11 as an illumination light source for observation, a condenser lens 12, an infrared light transmission filter 13, a flash lamp 15 as an illumination light source for photographing, a condenser lens 16, and a half mirror 17. The filter 13 is insertable between the lens 12 and the half mirror 17, and is removable therefrom, thereby shifting the illumination light for observation between infrared light and fixed light (visible light). Of course, instead of using the filter 13, an infrared light source may be provided further. In this case, a half mirror or a dichroic mirror may be used to combine an illumination optical path of the lamp 11 with that of the infrared light source, and these light sources may be controlled to light up selectively. The infrared or visible illumination light for observation from the lamp 11 passes through the lens 12, and is reflected by the half mirror 17 to converge on an entrance end face of the fiber 7. Further, visible illumination light for photographing from the lamp 15 passes through the lens 16, and is transmitted through the half mirror 17 to converge on the entrance end face of the fiber 7. A connector 8 is fixed on an exit end face of the fiber 7, and may be inserted into and removable from any one of a connecting portion of the photographing unit 1 and that of the illumination unit 2.

<Fundus Illumination Optical System>

Arranged in the photographing unit 1 is a fundus illumination optical system 20 constituted of a condenser lens 21, a ring slit 22, a focus chart 23, an illumination relay lens (a light-throwing lens) 24, and a half mirror 25. The chart 23 is made from a material transmitting visible light and infrared light, and its chart surface has a target mark formed thereon in a ring or cross shape, for example. The target mark is made of a coating having a wavelength property of transmitting visible light and cutting off infrared light. In addition, the chart 23 moves in a direction of an optical axis (a direction shown by an arrow) in synchronization with a focusing lens 33 of an observation/photographing optical system 30 which will be described later. A black absorber 26 absorbs the illumination light transmitted through the half mirror 25 to prevent noise light unnecessary for the observation/photographing optical system 30 from entering that system.

The illumination light for observation from the fiber 7 converges via the lens 21, and illuminates the slit 22 entirely. The light having passed through the slit 22 illuminates the chart 23, and proceeds to an eye E to be examined via the lens 24 and the half mirror 25. When the photographing unit 1 is positioned at a predetermined working distance, the light restricted to a ring shape by the slit 22 forms an image of the slit 22 in the vicinity of the pupil of the eye E, and then diffuses to illuminate a fundus Ef of the eye E as widely as or somewhat widely compared with a field of view for photographing.

In addition, the fundus illumination optical system 20 is used for both observation and photographing. The illumination light for photographing from the fiber 7 travels along the same optical path to illuminate the fundus Ef.

<Observation/Photographing Optical System>

Arranged in the photographing unit 1 is the observation/photographing optical system 30 constituted of an objective lens 31, a photographing diaphragm 32 placed at a position conjugate with the pupil of the eye E, the focusing lens 33, a photographing relay lens 34, a dichroic mirror 35, a color CCD camera 36 for photographing, an observation relay lens 37, a mirror 38 for turning a mirror image (a reversed image) back into an original image, and a CCD camera 39 for observation sensitive to a range from the visible region to the infrared region. The lens 33 may be moved in the direction of an optical axis L1 (a direction shown by an arrow) through a lens moving mechanism that is not illustrated. The travel of the lens 33 covers a range that allows fundus photographing of which base diopter is 0.00 D and even anterior segment photographing at a minimum lens-to-subject distance of +35 D. The dichroic mirror 35 has a property of reflecting infrared light and part of visible light but transmitting most of visible light. The visible light for photographing is transmitted through the dichroic mirror 35, and is received by the camera 36. Even in the case of color photographing, the camera 36 having a photographic element is capable of photographing with ten-times higher sensitivity than required for ordinary photography. Therefore, intensity of light from the lamp 15 may be lowered at the time of photographing.

<Slit Light Illumination Optical System>

Arranged in the illumination unit 2 is a slit light illumination optical system 40 constituted of a condenser lens 41, slit plates 42, filter plates 45, and illumination relay lenses (projecting lenses) 47 and 48. A plurality of the slit plates 42 with linear slits of different widths are prepared on a turret plate 43. By rotating the turret plate 43, one of the slit plates having a desired slit width may be selectively placed in an illumination optical path. In addition, the filter plates 45 include a cobalt filter, a green filter, and an aperture that allows the light therethrough intactly, all of which are prepared on a turret plate 46. Any one of them may be selectively placed in the illumination optical path as desired. The connector 8 of the fiber 7 is insertable into the connecting portion 2a of the illumination unit 2. The illumination light for observation and that for photographing from the fiber 7 illuminates the selected slit plate 42 via the lens 41. The light having passed through the slit plate 42 further passes through the selected filter plate 45, and proceeds to the eye E by the lenses 47 and 48 from a slanting direction.

Figure 4:
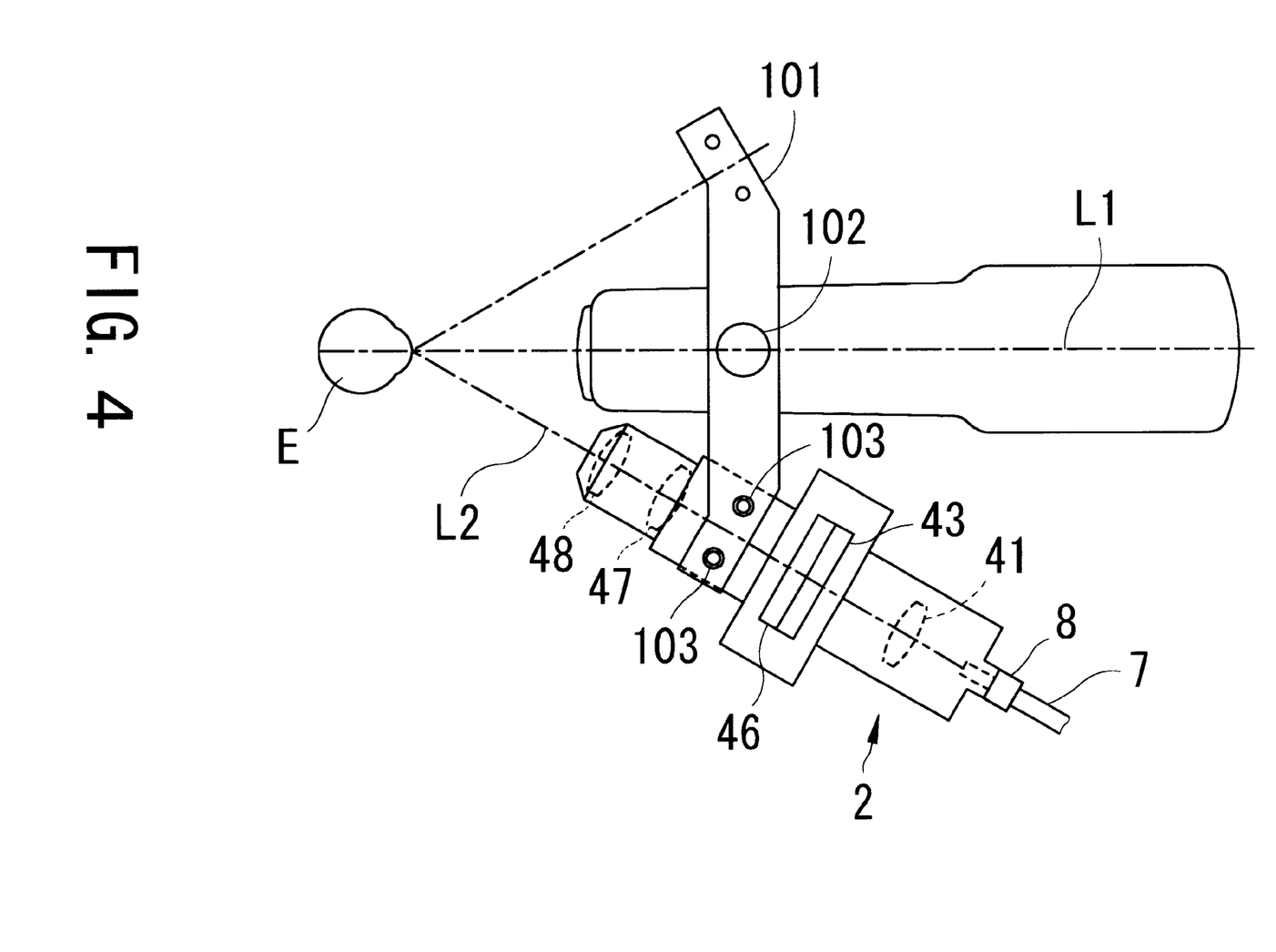
FIG. 4 shows the slit light illumination unit viewed from above when attached to the photographing unit.

FIG. 4 shows the illumination unit 2 viewed from above when attached to the photographing unit 1. A mounting plate 101 is attachable to and detachable from an upper part of the photographing unit 1. The mounting plate 101 is attached to the upper part of the photographing unit 1 with a screw 102. The mounting plate 101 has two arms, one of which extends rightward and the other leftward, and the illumination unit 2 may be hung to any one of the arms. FIG. 4 shows the illumination unit 2 mounted to the left arm of the mounting plate 101. The illumination unit 2 is mounted on the undersurface of the left arm of the mounting plate 101 with two revolving screws 103. The unit 2 is also mountable on the right arm of the mounting plate 101 with the two revolving screws 103.

The illumination unit 2 is designed to be mounted so that an optical axis L2 in the slit light illumination optical system 40 may be inclined 30 degrees toward the optical axis L1 in the observation/photographing optical system 30. In addition, the illumination unit 2 is also set to be mounted so that a slit-image forming position may correspond to a proximate position at which the whole anterior segment of the eye E may be photographed in appropriate size by means of the observation/photographing optical system 30. Specifically, in the present apparatus, it is arranged that the slit-image forming position should coincide with a focal point of the lens 33 placed at a +35 D focus position. In the above description, the optical axis L2 is defined as having a 30-degree angle of projection from the side. However, as a matter of course, the angle setting is not limited thereto, and should be determined as necessary for making diagnosis.

Figure 5:
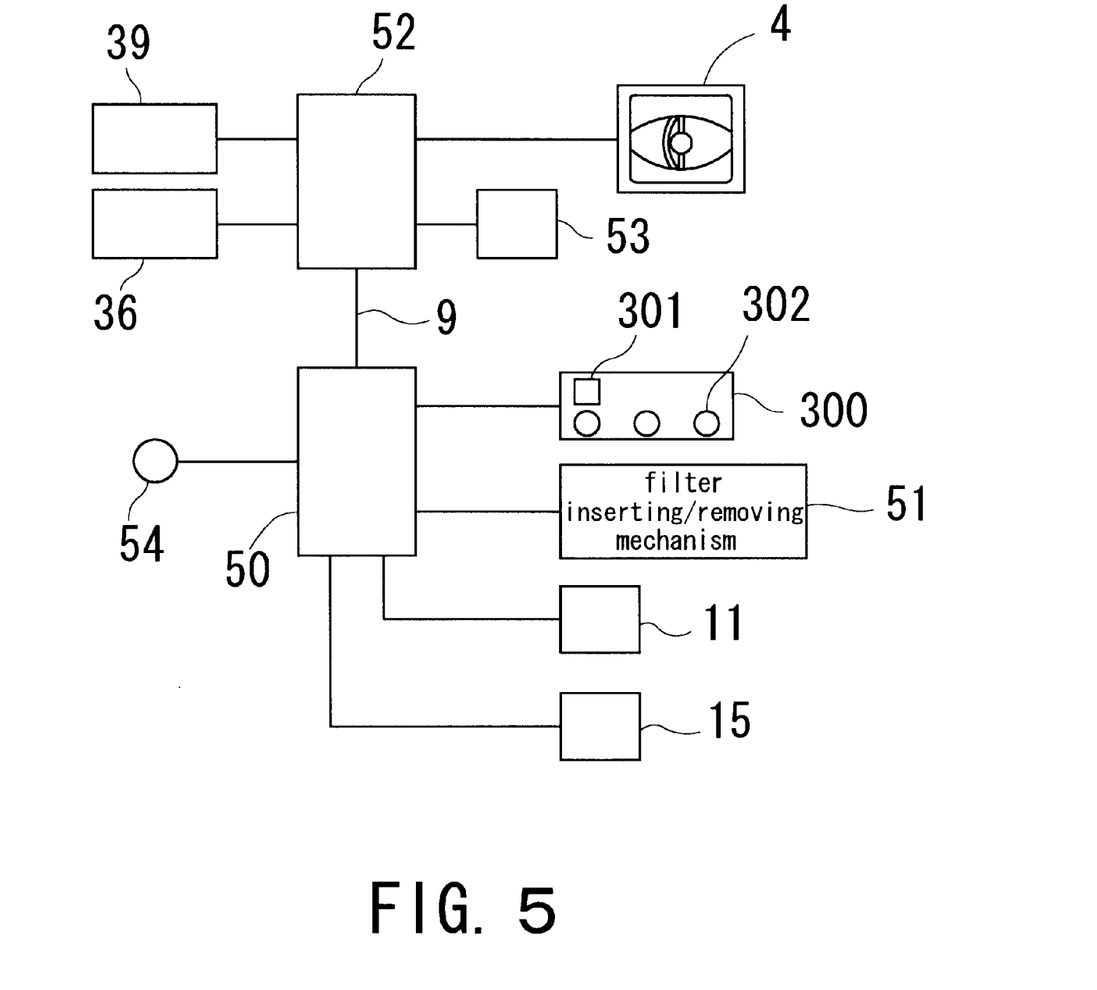
FIG. 5 is a block diagram of a control system in the present ophthalmic photographing apparatus.

A description will now be given to operation of the apparatus configured as above, referring to a block diagram of a control system shown in FIG. 5.

To photograph a fundus Ef, as shown in FIG. 2, the connector 8 of the fiber 7 is inserted into a connecting portion of the photographing unit 1. For non-mydriasis photographing, a non-mydriasis photographing mode should be selected using a switch 301 included in the control panel 300 of the control unit 3. When this mode is selected, a main control part 50 drives a filter inserting/removing mechanism 51 to place the filter 13 in the illumination optical path of the lamp 11.

After lighting the lamp 11 using a switch 302, the examiner holds the grip part 1*a* of the photographing unit 1 with his hand. Then, from a short distance before the eye E, he moves the photographing unit 1 nearer to the eye E, so that the infrared illumination light for observation illuminates the eye E. The light reflected from the eye E (the fundus Ef) passes through the half mirror 25, the lens 31, the diaphragm 32, and the lenses 33 and 34, and is then reflected by the dichroic mirror 35 to form an image on a photographic element of the camera 39 via the lens 37. Picture signals from the camera 39 are inputted to an image control part 52, and a fundus image (an image for observation) is then displayed as a moving image on the monitor 4 connected to the image control part 52.

In the image for observation displayed on the monitor 4, the target mark on the chart 23 can be recognized as a black shadow. Therefore, the examiner moves the lens 33 to focus on the fundus Ef so that an image of the target mark may be brought into focus. After the focusing, a photographing switch 54 is pressed to cause the main control part 50 to light the lamp 15. The visible illumination light for photographing illuminates the fundus Ef, and the light reflected from the fundus Ef passes through the half mirror 25, the lens 31, the diaphragm 32, and the lenses 33 and 34, and is transmitted through the dichroic mirror 35 to form an image on a photographing element of the camera 36. Picture signals from the camera 36 are inputted to the image control part 52 to undergo A/D conversion, and are stored in an image memory 53. Then the image is displayed as a color still-frame image on the monitor 4.

As described above, non-mydriatic fundus photographing may be performed with the fundus Ef observed under infrared illumination light for observation. Moreover, mydriatic fundus photographing may also be performed with a mydriatic administered and the fundus Ef thereby observed under visible illumination light for observation. In this case, the apparatus is set in a mydriasis photographing mode, and the filter 13 is removed from the illumination optical path of the lamp 11. Since the visible light reflected from the eye E (the fundus Ef) also forms an image in the camera 39, the fundus image (the image for observation) is displayed as a moving image on the monitor 4.

Next, a description will now be given to photographing a slit-sectioned anterior segment of the eye E using the illumination unit 2. In this case, as shown in FIG. 4, the illumination unit 2 is attached to the photographing unit 1 via the mounting plate 101. The connector 8 of the fiber 7 is then disconnected from the photographing unit 1, and is inserted into the connecting portion 2*a* of the illumination unit 2. In the present apparatus, the use of the illumination unit 2 makes it possible to perform slit-sectioned anterior segment photographing under either mydriatic or non-mydriatic conditions.

For the mydriatic, slit-sectioned anterior segment photographing, the mydriasis photographing mode is selected using the switch 301. In this mode, the filter 13 is removed from the illumination optical path of the lamp 11 through the filter inserting/removing mechanism 51. After lighting the lamp 11 using the switch 302, the examiner holds the grip part 1*a* of the photographing unit 1 with his hand, and faces it toward the eye E. The fiber 7 transmits the visible illumination light for observation from the lamp 11 to the slit light illumination optical system 40 in the illumination unit 2, where the light proceeds to the eye E. The turret plates 43 and 46 are rotated as needed to select from among the slit widths and among the filters (or the aperture) as desired.

The visible light scattered from the anterior segment of the eye E forms an image on the photographic element of the camera 39 by means of the observation/photographing optical system 30. The camera 39 picks up an image of the anterior segment (an image for observation), which is then displayed on the monitor 4 in the same manner as at the time of photographing a fundus Ef. It should be noted that in the mydriasis photographing mode, the image control part 52 may process the picture signals from the camera 36 to display the image of the anterior segment (the image for observation) on the monitor 4. In this case, the monitor 4 shows a color moving image.

The examiner observes the image of the anterior segment on the monitor 4 to make adjustments for the slit light to be projected onto a desired part of the eye E. The lens 33 is moved to a specified position in advance to arrange that the focal point on the part to be photographed coincide with the slit-image forming position. Then, at the press of the switch 54, the lamp 15 emits the visible illumination light for photographing, which illuminates the anterior segment through the slit via the fiber 7 and the slit illumination optical system 40. The camera 36 then picks up an image of the slit-illuminated anterior segment. Picture signals from the camera 36 are stored in the image memory 53, and the image is then displayed as a color still-frame image on the monitor 4.

For the non-mydriatic, slit-sectioned anterior segment photographing, the non-mydriasis photographing mode is selected using the switch 301. In this mode, the filter 13 is placed in the illumination optical path of the lamp 11. The optical fiber 7 transmits the infrared illumination light for observation from the lamp 11 to the slit illumination optical system 40 in the illumination unit 2, where the light proceeds to the eye E. Since the iris of the eye E reflects the infrared illumination light for observation, the camera 39 picks up an image of a portion of the iris which is slit-illuminated, and the image is displayed on the monitor 4. The examiner observes the image of the iris portion displayed on the monitor 4 to perform alignment. Then, at the press of the switch 54, the lamp 15 emits the visible illumination light for photographing, which illuminates the anterior segment through the slit via the fiber 7 and the slit illumination optical system 40. The camera 36 picks up an image of the anterior segment which is slit-illuminated. Since the infrared illumination light for observation is invisible, the anterior segment may be slit-photographed with its pupil open in a dark place. Picture signals from the camera 36 are stored in the image memory 53, and the image is then displayed as a color still-frame image on the monitor 4.

Since the apparatus is configured as described above, the apparatus is capable of photographing a slit-sectioned anterior segment as well as a fundus, thereby serving many purposes in ophthalmic examinations. In particular, since the apparatus is capable of photographing a fundus and a slit-sectioned anterior segment under non-mydriatic conditions, it is unnecessary to use stimulating visible light and mydriatics, thereby placing little burden on a patient. In addition, its excellent portability makes it useful not only for doctor's house calls or rounds of hospital rooms, but also for diagnosis and treatment given at small, under-equipped clinics, including those in the outlands.

In the above description, the monitor 4 of the control unit 3 is used for observation and checking of a photographed image. Alternatively, a small monitor may be installed on the photographing unit 1.

Also, in the above description, the infrared illumination light for observation is obtained from the halogen lamp 11 and the infrared filter 13 placed in the control unit 3. Instead, an infrared light source for observation may be provided alone. In this case, the apparatus may be used only in the non-mydriasis photographing mode.

Figure 6:
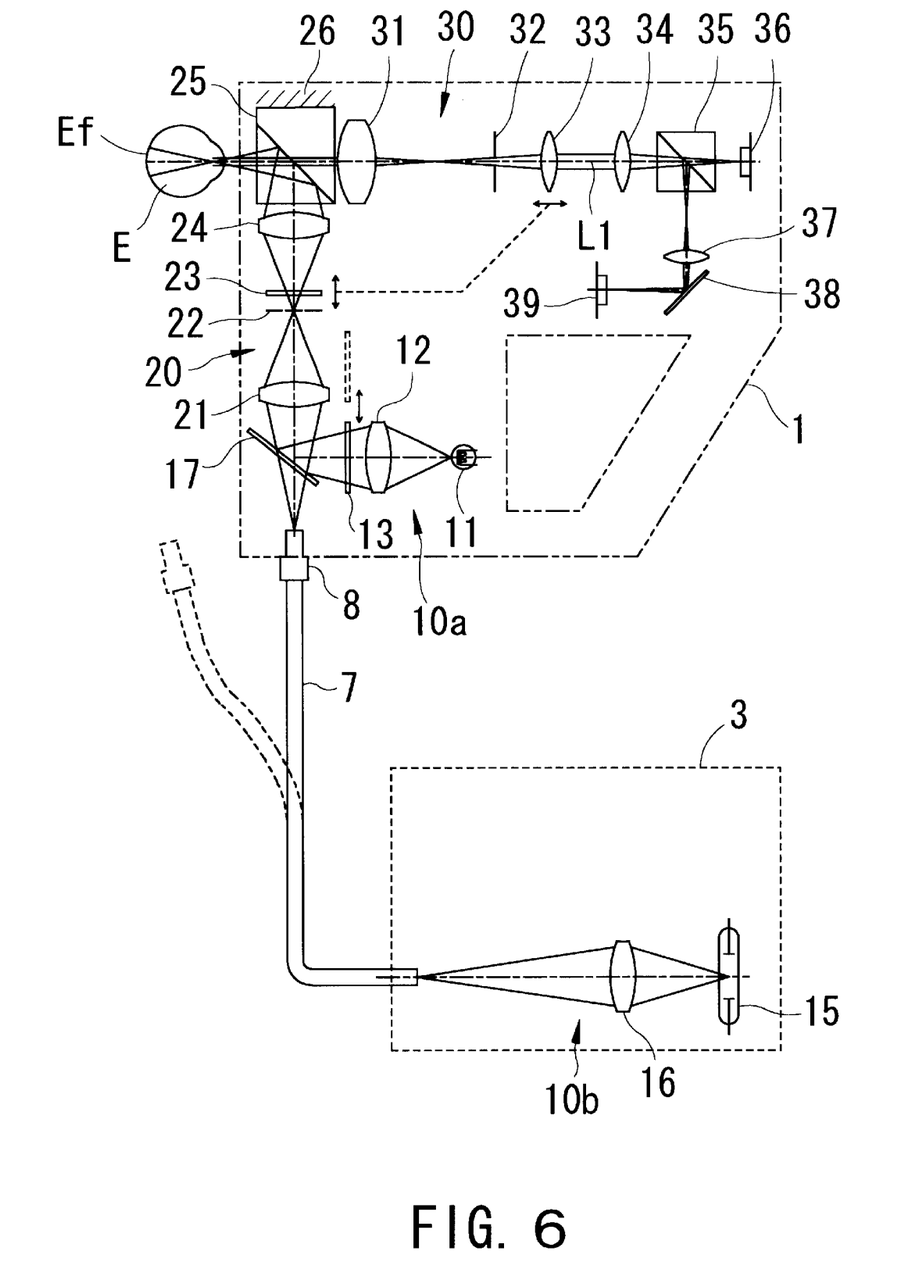
FIG. 6 shows a modification of the optical systems in the photographing unit and in the control unit.

As shown in FIG. 6, the photographing unit 1 may include the lamp 11, the lens 12, the filter 13, and the half mirror 17 (an illumination light source optical system for observation 10a), while the control unit 3 may include only the lamp 15 and the lens 16 (an illumination light source optical system for photographing 10b).

As described up to this point, according to the present invention, fundus photographing and anterior segment slit-photographing may be performed in non-mydriatic conditions.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic photographing apparatus comprising:
   a light source unit in which an infrared illumination light source optical system for observation and a visible illumination light source optical system for photographing are placed;
   a hand-held photographing unit in which a first illumination optical system having an illumination lens and an observation/photographing optical system having an objective lens are placed, the photographing unit being separated from the light source unit;
   a slit light illumination unit in which a second illumination optical system having a slit plate and an illumination lens is placed, the illumination unit being removably attached to the photographing unit; and
   a photoconductive tube which connects the light source unit selectively to any one of the photographing unit and the illumination unit and which transmits infrared illumination light for observation and visible illumination light for photographing from the light source unit selectively to any one of the first illumination optical system and the second illumination optical system;
   wherein the observation/photographing optical system is used to observe and photograph a fundus of an eye to be examined which is illuminated by the infrared illumination light for observation and the visible illumination light for photographing via the first illumination optical system, and to observe and photograph an anterior segment of the eye illuminated by the infrared illumination light for observation and the visible illumination light for photographing via the second illumination optical system.

2. The ophthalmic photographing apparatus according to claim 1, wherein
   a visible illumination light source optical system for observation is placed further in the light source unit, and
   the observation/photographing optical system is used to observe the fundus illuminated by visible illumination light for observation via the first illumination optical system, and to observe the anterior segment illuminated by the visible illumination light for observation via the second illumination optical system.

3. The ophthalmic photographing apparatus according to claim 2, wherein the infrared illumination light source optical system for observation and the visible illumination light source optical system for observation share a visible light source.

4. The ophthalmic photographing apparatus according to claim 1, wherein the illumination unit is attached to the photographing unit in such a manner that an optical axis of the second illumination optical system have a predetermined angle of inclination with respect to an optical axis of the observation/photographing optical system.

5. The ophthalmic photographing apparatus according to claim 1, wherein the observation/photographing optical system includes an observation optical system having a photographic element for observation and a photographing optical system having a photographic element for photographing and sharing part of an optical path with the observation optical system.

6. An ophthalmic photographing apparatus comprising:
   a light source unit in which a visible illumination light source optical system for photographing is placed;
   a hand-held photographing unit in which an infrared illumination light source optical system for observation, a first illumination optical system having an illumination lens, and an observation/photographing optical system having an objective lens are placed, the photographing unit being separated from the light source unit;
   a slit light illumination unit in which a second illumination optical system having a slit plate and an illumination lens is placed, the illumination unit being removably attached to the photographing unit; and a photoconductive tube which connects the light source unit selectively to the photographing unit and the illumination unit and which transmits visible illumination light for photographing from the light source unit selectively to the first illumination optical system and the second illumination optical system;

wherein the observation/photographing optical system is used to observe and photograph a fundus of an eye to be examined which is illuminated by infrared illumination light for observation and the visible illumination light for photographing via the first illumination optical system, to observe an anterior segment of the eye illuminated by infrared illumination light for observation via the first illumination optical system, and to photograph the anterior segment illuminated by the visible illumination light for photographing via the second illumination optical system.

7. The ophthalmic photographing apparatus according to claim 6, wherein a visible illumination light source optical system for observation is placed further in the photographing unit, and the observation/photographing optical system is used to observe the fundus and the anterior segment, each of which is illuminated by visible illumination light for observation via the first illumination optical system.

8. The ophthalmic photographing apparatus according to claim 7, wherein the infrared illumination light source optical system for observation and the visible illumination light source optical system for observation share a visible light source.

9. The ophthalmic photographing apparatus according to claim 6, wherein the illumination unit is attached to the photographing unit in such a manner that an optical axis of the second illumination optical system have a predetermined angle of inclination with respect to an optical axis of the observation/photographing optical system.

10. The ophthalmic photographing apparatus according to claim 6, wherein the observation/photographing optical system includes an observation optical system having a photographic element for observation and a photographing optical system having a photographic element for photographing and sharing part of an optical path with the observation optical system.

* * * * *